United States Patent [19]

Oyama et al.

[11] Patent Number: 5,191,102

[45] Date of Patent: Mar. 2, 1993

[54] PROCESS OF PRODUCING SILETHYLENE OXIDE

[75] Inventors: Masayuki Oyama, Takasaki; Kenichi Fukuda, Annaka; YAsushi Yamamoto, Takasaki; Noriyuki Koike, Gunma, all of Japan

[73] Assignee: Shin-Etsu Chemical Co. Ltd., Tokyo, Japan

[21] Appl. No.: 913,345

[22] Filed: Jul. 15, 1992

[30] Foreign Application Priority Data

Jul. 16, 1991 [JP] Japan .................. 3-201322

[51] Int. Cl.$^5$ ............................... C07F 7/08
[52] U.S. Cl. ..................... 556/464; 556/434
[58] Field of Search .................. 556/464, 434

[56] References Cited

U.S. PATENT DOCUMENTS

| | | | |
|---|---|---|---|
| 4,535,174 | 8/1985 | Crivello | 556/464 X |
| 4,675,426 | 6/1987 | Givello | 556/464 |
| 5,118,828 | 6/1992 | Takago et al. | 556/464 X |

Primary Examiner—Paul F. Shaver

Attorney, Agent, or Firm—Oblon, Spivak, McClelland, Maier & Neustadt

[57] ABSTRACT

A process of producing a silethylene oxide represented by the following general formula (1):

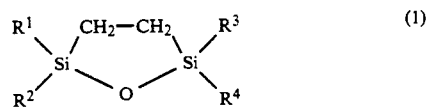

wherein $R^1$, $R^2$, $R^3$, and $R^4$ each represent a hydrocarbon group having 1 to 8 carbon atoms such as a methyl group, comprising the steps of thermally decomposing the hydrolyzate of 1,4-dichloro-1,1,4,4-tetrahydrocarbyl-1,4-disilabutane in the presence of an alkali, bringing the thermally decomposed product in contact with carbon dioxide and distilling the reaction mixture. According to this process, in the distillation, since polymerization or formation of 2,5-disilahexane-2,5-diol can be obviated, a purified silethylene oxide can be obtained in high yield. Further, the distillation apparatus will not be clogged with by-products.

3 Claims, No Drawings

PROCESS OF PRODUCING SILETHYLENE OXIDE

BACKGROUND OF THE INVENTION

1. Field of the Invention

The present invention relates to a process of producing a silethylene oxide in high yield.

2. Description of the Prior Art

Hitherto, to produce a silethylene oxide represented by the following formula:

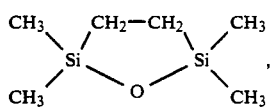

dimethylchlorosilane and dimethylchlorovinylsilane are subjected to an addition reaction, followed by hydrolysis and then thermal decomposition in the presence of an alkali (J. Am. Chem. Soc. 82, 1883 (1960), U.S. Pat. No. 3,041,362, and J. Poly. Sci. 12, 1089 (1974)).

This process is attended with problems, for example, first since the reaction mixture after the thermal decomposition reaction is in admixture with the alkali, the subsequent purification by distillation readily results in polymerization of the silethylene oxide to lower the yield of the silethylene oxide considerably, which sometimes yields no silethylene oxide at all, or even if a silethylene oxide is obtained, since the alkali is in admixture with the silethylene oxide, similar polymerization of the silethylene oxide takes place during the storage in some cases. Secondly since the alkali is used in the form of an aqueous solution and water used for the aqueous solution is incorporated in the reaction product, the water reacts readily with the silethylene oxide during the storage or at the time of the purification by distillation to form solid 2,5-disilahexane-2,5-diol to lower the yield or to clog the inside of the distillation apparatus.

SUMMARY OF THE INVENTION

Therefore, an object of the present invention is to provide a process of producing a silethylene oxide in high yield which is free of the above problems caused by the incorporation of an alkali or water.

According to the present invention, in a process of producing a silethylene oxide represented by the following general formula (1):

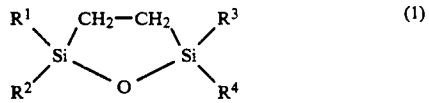

wherein $R^1$, $R^2$, $R^3$, and $R^4$, which may be the same or different, each represent an unsubstituted or substituted hydrocarbon group having 1 to 8 carbon atoms, which comprises hydrolyzing 1,4-dichloro-1,1,4,4-tetrahydrocarbyl-1,4-disilabutane and then by thermally decomposing the resulting reaction mixture in the presence of an alkali, the improvement comprising the steps of bringing the reaction mixture obtained in the thermal decomposition in contact with carbon dioxide and distilling the obtained reaction mixture.

The present invention has succeeded in attaining the above-mentioned object by performing the neutralization of the reaction product with carbon dioxide prior to the distillation.

DETAILED DESCRIPTION OF THE INVENTION

In the above general formula (1) representing the silethylene oxide which is the intended product of the present invention, specific examples of the hydrocarbon groups $R^1$, $R^2$, $R^3$, and $R^4$ having 1 to 8 carbon atoms include an alkyl group such as a methyl group, an ethyl group, a propyl group, an isopropyl group, a butyl group, an isobutyl group, and a t-butyl group, an aryl group such as a phenyl group, and a halogenated alkyl group such as a trifluoropropyl group. In particular, an alkyl group is preferable, and the present invention is particularly suitable for producing, for example, a silethylene oxide represented by the general formula (1) wherein each of $R^1$, $R^2$, $R^3$, and $R^4$ is the methyl group.

Starting Raw Material

The 1,4-dichloro-1,1,4,4-tetrahydrocarbyl-1,4-disilabutane used as a raw material in the present invention is synthesized by the addition reaction between a dicarbylchlorosilane and a vinylchlorodicarbylsilane. This addition reaction is represented by the following equation:

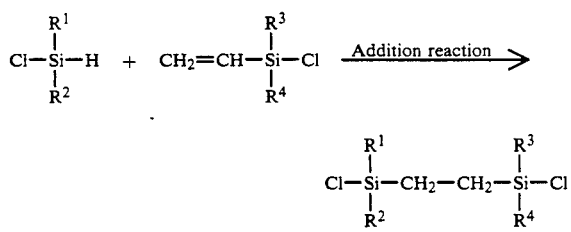

wherein $R^1$, $R^2$, $R^3$, and $R^4$ represents groups respectively corresponding to $R^1$, $R^2$, $R^3$, and $R^4$ in the above general formula (1).

This addition reaction is carried out generally in the presence of a platinum catalyst such as platinum without a solvent or in a solvent such as toluene at 50° to 120° C.

Hydrolysis

In the present invention, the above-mentioned 1,4-dichloro-1,1,4,4-tetrahydrocarbyl-1,4-disilabutane (hereinafter referred to as dichlorodisilabutane) is hydrolyzed to obtain a disilanol wherein the terminal chlorine atoms of the above dichlorodisilabutane have been replaced with hydroxyl groups.

This hydrolysis proceeds quickly by mixing the dichlorodisilabutane with excess water. For example, if the synthesis of the dichlorodisilabutane and its hydrolysis are carried out continuously, it is recommended that the reaction mixture after the completion of the above addition reaction is added to a large amount of cooled water preferably having a temperature of 0° to 15° C.

Thermal Decomposition

According to the present invention, by thermally decomposing the disilanol obtained in the above hydrolysis in the presence of an alkali, a silethylene oxide represented by the above general formula (1) is produced.

Desirably, this thermal decomposition is carried out in an atmosphere of an inert gas such as nitrogen and suitably the heating temperature is 200° to 600° C. As the alkali, for example, NaOH, KOH, or CsOH is preferably used and the amount of the alkali to be used is desirably in the range of 0.1 to 20% by weight in terms of the alkali metal based on the above disilanol. The alkali is used as an aqueous solution generally having a concentration of about 5 to 60%.

This thermal decomposition is carried out by using the mixture obtained by hydrolyzing the above dichlorodisilabutane as it is, wherein the water is distilled off with the production of the intended silethylene oxide.

Neutralization and Distillation

In the present invention, the thus obtained thermally decomposed product containing the silethylene oxide is brought in contact with carbon dioxide, so that the employed alkali is neutralized. There is no particular restriction on how carbon dioxide is brought in contact with the reaction mixture, and, for example, carbon dioxide in the gaseous state may be passed through the reaction mixture, or carbon dioxide in the state of dry ice may be charged into the reaction mixture.

The amount of carbon dioxide to be used is the equivalent molar amount or more to the molar amount of the alkali in the reaction mixture.

The temperature of the carbon dioxide which is brought in contact with the reaction mixture is preferably 0° C. or below, more preferably −10° C. or below. When carbon dioxide is charged at such a low temperature, the water in the reaction mixture freezes into bulky masses, which are liable to float on the reaction mixture surface. In this regard, it is preferable to use the technique wherein carbon dioxide in the state of dry ice is charged. The thus frozen water can be readily removed by filtering, which means that any particular device is not required.

The neutralized reaction mixture is subjected to distillation. Thus since the reaction mixture is already neutralized and dehydrated, polymerization does not take place in the distillation, and an unfavorable reaction, for example, a reaction wherein 2,5-disilahexane-2,5-diol is produced will not occur. Consequently, any procedure of eliminating by-products is not required in the distillation and the intended silethylene oxide can be obtained in high yield.

EXAMPLES

Example 1

930 g of a product (having a disilanol content of 6 mol %) obtained by hydrolyzing 1,4-dichloro-1,1,4,4-tetramethyl-1,4-disilabutane was mixed with 37.2 g of 50% aqueous potassium potassium hydroxide solution, followed by stirring, and then the resulting mixture was subjected to a thermal decomposition at 370° C. in an nitrogen atmosphere. After the reaction, 75 g of dry ice was charged into the reaction mixture. The thus frozen water was filtered off to obtain 690 g of a reaction mixture. When the obtained reaction mixture (containing 74.5% of the intended product) was distilled, 500 g of a silethylene oxide (having a purity of 94.5%) represented by

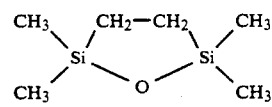

was obtained (yield: 91.9%).

Comparative Example 1

296 g of a product (having a disilanol content of 4 mol %) obtained by hydrolyzing 1,4-dichloro-1,1,4,4-dimethyl-1,4-disilabutene was mixed with 4 g of 50% aqueous potassium hydroxide solution, followed by stirring, and after the resulting mixture was thermally decomposed at 270° C. in a nitrogen atmosphere, 209 g of a reaction mixture (containing 48.4% of the intended product) was obtained. When the reaction mixture was subjected to distillation, a polymerization took place in the distillation flask, so that the intended silethylene oxide was not obtained at all.

We claim:

1. In a process of producing a silethylene oxide represented by the following general formula (1):

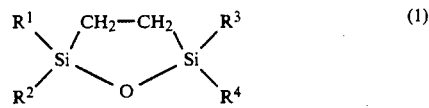

wherein $R^1$, $R^2$, $R^3$, and $R^4$, which may be the same or different, each represent an unsubstituted or substituted hydrocarbon group having 1 to 8 carbon atoms, which comprises hydrolyzing 1,4-dichloro-1,1,4,4-tetrahydrocarbyl-1,4-disilabutane and then thermally decomposing the resulting reaction mixture in the presence of an alkali, the improvement comprising the steps of bringing the reaction mixture obtained in the thermal decomposition in contact with carbon dioxide and distilling the obtained reaction mixture.

2. A process as claimed in claim 1, wherein said carbon dioxide is in the form of dry ice, and said distillation is carried out after filtering off the water frozen by bringing the dry ice in contact with the reaction mixture.

3. A process as claimed in claim 1, wherein, in the general formula (1), $R^1$, $R^2$, $R^3$, and $R^4$ are each the methyl group.

* * * * *